United States Patent
Burkhart

(10) Patent No.: US 6,537,308 B2
(45) Date of Patent: *Mar. 25, 2003

(54) COSMETIC AND THERAPEUTIC FACE MASK

(76) Inventor: Alma D. Burkhart, 1448 Ryan Ct., Grapevine, TX (US) 76051

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/549,288

(22) Filed: Apr. 14, 2000

(65) Prior Publication Data
US 2003/0014096 A1 Jan. 16, 2003

(51) Int. Cl.⁷ .................................................. A61F 7/00
(52) U.S. Cl. ..................... 607/109; 607/114; 607/112; 604/303; 2/171.2
(58) Field of Search ................................ 607/109, 140, 607/141, 108, 110, 111, 112, 114; 2/206, 171.2; 604/303

(56) References Cited

U.S. PATENT DOCUMENTS

| | | | |
|---|---|---|---|
| 2,874,385 A | * 2/1959 | Wade | 2/15 |
| 3,211,146 A | 10/1965 | Rodelli | |
| 3,354,884 A | 11/1967 | Rudo | |
| 4,372,318 A | * 2/1983 | Viesturs et al. | 128/403 |
| 5,099,829 A | 3/1992 | Wu | 128/32 |
| 5,169,384 A | * 12/1992 | Bosniak et al. | 604/20 |
| 5,395,400 A | * 3/1995 | Stafford et al. | 607/109 |
| 5,507,794 A | * 4/1996 | Allen | 607/112 |
| 5,623,733 A | 4/1997 | Kurimoto et al. | 2/206 |
| 5,628,772 A | * 5/1997 | Russell | 607/109 |
| 5,665,057 A | * 9/1997 | Murphy | 602/19 |
| 5,700,238 A | 12/1997 | Hyson | 602/74 |
| 5,823,984 A | * 10/1998 | Silverberg | 602/61 |
| 5,879,379 A | * 3/1999 | Mason et al. | 607/109 |
| 5,928,262 A | 7/1999 | Harber | 606/204.35 |
| 5,928,275 A | * 7/1999 | Yates et al. | 607/112 |
| 5,971,947 A | * 10/1999 | McNally et al. | 602/62 |
| 6,193,740 B1 | * 2/2001 | Rodriguez | 606/204.15 |

* cited by examiner

Primary Examiner—Linda C. M. Dvorak
Assistant Examiner—Jocelyn Ram
(74) Attorney, Agent, or Firm—Charles D. Gunter, Jr.

(57) ABSTRACT

A washable facial mask comprising a unitary frontal element having two eye patch regions made from a washable material, the two eye patch regions coupled to straps having a fastening means for securing the eye patch regions over the eyes of a person, the straps being made from a washable material. The eye patch regions have a pocket means for allowing placement of facial contact elements, the pocket means also made from a washable material.

8 Claims, 1 Drawing Sheet

COSMETIC AND THERAPEUTIC FACE MASK

BACKGROUND OF THE INVENTION

1. Field of the Invention

The present invention relates in general to a facial mask, and in particular to a mask for placing therapeutic and/or cosmetic items upon the eyes of a person, for example, while they are sleeping, the mask being washable and permeable.

2. Description of the Prior Art

It is often desirable to apply therapeutic agents and remedies to the face, and in particular to apply these agents for an extended period of time. Simply holding, by hand, the agent and its carrier to one's face is impractical and uncomfortable for extended periods. In particular, it is often desirable to apply such agents, such as chemical agents or hot or cold compresses, overnight during one's sleep. This makes the need for a facial mask particularly important.

There are several types of facial masks in the prior art. For example, Rodelli (U.S. Pat. No. 3,211,146) discloses a full facial mask made from non-porous rubber and the like used for applying medications to the face. A cosmetic face mask is disclosed by Rudo (U.S. Pat. No. 3,354,884) that has eye openings cut into the mask and is designed primarily to apply pressure to the face in order to reduce puffiness of the skin and deliver moisturizers by impregnating a pad attached to the inside of the mask. Wu (U.S. Pat. No. 5,099,829) discloses a mask that presses electrical-stimulating elements against certain portions of the face around the eyes as an acupuncture therapy. A mask for headaches is disclosed by Hyson (U.S. Pat. No. 5,700,238), wherein a rigid segment forms a mask having a plurality of gauze-like formations on the skin-facing side for administering medications. Finally, Kurimoto et al. (U.S. Pat. No. 5,623,733) discloses a full-face and neck mask for applying moisturizer to the face and neck, the mask having numerous straps and fasteners for applying to the head of a person.

One drawback to the prior art face masks is that most are not washable. Another drawback to the prior art is that the materials used in the mask make it difficult to wear comfortably while sleeping. Further, many are difficult to use, having numerous straps and made such that sleeping while wearing the mask is made even more difficult. Also, most of the prior art masks are not versatile enough to allow for the use of a range of therapies such as moisturizer, aromatherapy materials, and hot or cold compresses.

In particular, it has become more common to use aromatherapy as a beauty agent as well as to enhance one's well-being. Most aromatherapy works by applying an "essential" oil from various plants such as basil, lavander, chamomile, and the like to various external portions of the body, and/or to breathe the oils. It is believed that the oils are taken in by the body through the blood vessels within the nasal passageways and lungs, and have been used for centuries.

What is needed is an improved method of applying these aromatherapy agents and other agents to the face and in particular to the eye region of a person while sleeping. The prior art masks are not well suited to apply an agent to the skin, while being permeable enough to allow aromas and gases to flow through the mask so that they may also be breathed. Further, it is desirable to attain these objects in a washable mask. The present invention is directed to such a need.

SUMMARY OF THE INVENTION

It is one object of the present invention to provide facial mask that is washable.

It is yet another object of the present invention to provide a facial mask that is permeable to therapeutic agents such as in aromatherapy.

It is yet another object of the present invention to provide a facial mask that is simple and easy to use for various functions such as the application of therapeutic agents, beauty treatments, cosmetic treatments and cold or hot compresses against a person's face.

These and other objects are achieved by providing a washable facial mask that can be used comfortably while sleeping, the mask used for holding facial contact elements such as sewn bags containing therapeutic materials against a person's face, and in particular at the eye region. In particular, aromatherapy agents can be administered using the mask, wherein the oils are placed within the facial contact elements. The facial contact elements can also be cold or hot compress bags, or may simply be padded bags for comfort. The facial mask comprises a unitary frontal element having two eye patch regions made from a washable material such as silk, cotton, or satin. Both the frontal element and the eye patch regions may be made from the same material, and sewn together in layers, or as a one-layer unit. There may also be padding between layers of material used for the frontal element.

The two eye patch regions are coupled to straps having a fastening means for securing the mask over the head of the person, thus holding the eye patch regions over the person's eyes. The straps are typically made from a washable material similar to the material for the frontal element and eye patch regions. Typically, the straps are also in unity—being cut from the same cloth material—with the frontal element. The frontal element or eye patch regions may be opaque or translucent, depending upon the color, thickness, and layering of the materials used.

The eye patch regions have a pocket means for allowing placement of facial contact elements, the pocket means also made from a washable material. Typically, the eye patch regions are a washable, mesh material that allows free egress and permeability of moisture, vapor, and is non-insulating. The primary function of the pocket means is to secure and hold facial contact elements such as bags and the like within the mask, which is then in turn held against the eyes of a person wearing the facial mask.

Additional objects, features and advantages will be apparent in the written description which follows.

BRIEF DESCRIPTION OF THE DRAWINGS

The novel features believed characteristic of the invention are set forth in the appended claims. The invention itself however, as well as a preferred mode of use, further objects and advantages thereof, will best be understood by reference to the following detailed description of an illustrative embodiment when read in conjunction with the accompanying drawings, wherein:

DESCRIPTION OF THE INVENTION

The present invention is washable facial mask that can be used for holding facial contact elements such as sewn bags containing therapeutic materials against a person's face, and in particular at the eye region. Cosmetic or beauty treatments such as cucumber slices, vegetable or fruit seeds, moisturizers, etc. may also constitute the facial contact element. The facial contact elements can also be cold or hot compress bags, or may simply be padded bags for comfort. The facial mask comprises a unitary frontal element having two eye patch regions made from a washable material. Both the frontal element and the eye patch regions may be made from the same material, and sewn together in layers, or as a one-layer unit. There may also be padding between layers of material used for the frontal element.

The two eye patch regions are coupled to straps having a fastening means for securing the eye patch regions over the eyes of a person. The straps are typically made from a washable material similar to the material for the frontal element and eye patch regions. Typically, the straps are also in unity—being cut from the same cloth material as one piece—with the frontal element.

The eye patch regions have a pocket means for allowing placement of facial contact elements, the pocket means also made from a washable material. Typically, the eye patch regions are a washable, mesh material that allows free egress and permeability of moisture, vapor, and is non-insulating. The primary function of the pocket means is to secure and hold facial contact elements such as bags and the like within the mask, which is then in turn held against the eyes of a person wearing the facial mask.

The eye patch regions may be translucent or opaque, depending upon the desired application and type and layers of fabric or cloth material used. The materials used to make the facial mask are typically such materials selected from a group comprising silk, nylon, satin and cotton. Silk, due to its comfort and ease of washing, is a preferable fabric to use. One embodiment of the facial contact elements are sealed cloth bags such as silk material sewn into a closed bag. The removable and exchangeable bags typically contain a therapeutic material such a oils used in aromatherapy, moisturizers, facial beauty treatments such as cucumber slices and other vegetable slices or seeds, and other agents. In another embodiment, the facial contact elements are variable temperature elements such as PVC bags containing liquids that can be cooled to thus provide a cooling effect to the person wearing the mask, or bags that contain heated material to apply heat to the person wearing the mask.

Figure 1:
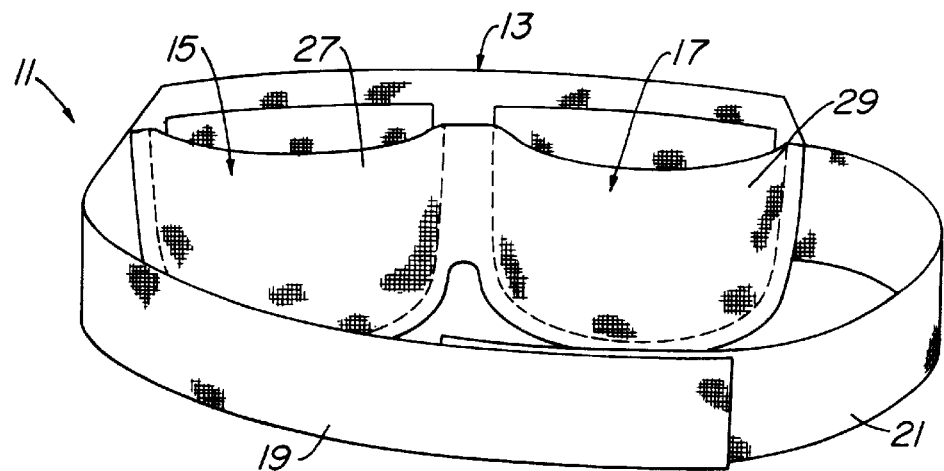
FIG. 1 is a perspective rear-view of the face mask of the invention.

The invention is more particularly described with reference to the figures, and first with FIG. 1, wherein the mask 11 is shown in detail from a rear view. A unitary frontal element 13 comprising two eye patch regions 15 and 17 are made from a washable material. Washable materials are such materials as cotton, silk, nylon, satin, wool, or other natural or synthetic, woven or non-woven materials that form a flexible, translucent or opaque barrier. Materials such as silk and satin are preferable, as the unitary frontal element will be placed against the face of the person who wears the mask, thus the comfort of the material is a useful advantage.

Coupled to the unitary frontal element are straps 19 and 21, wherein fastening means can be attached. The straps are typically of such a length that they can be wrapped around a person's head, thus holding the eye patch regions 15 and 17 against the eyes and surrounding orbital and buccal (cheek) region. Secured to the eye patch regions are the pocket means 27 and 29, respectively, which make direct contact with the person's skin. The pocket means 27 and 29 are typically made from a synthetic mesh material such as nylon mesh of such a porosity as to allow free permeability of gases and moisture between the mesh in communication between the person's skin and facial contact elements within the pocket means 27 and 29.

Figure 2:
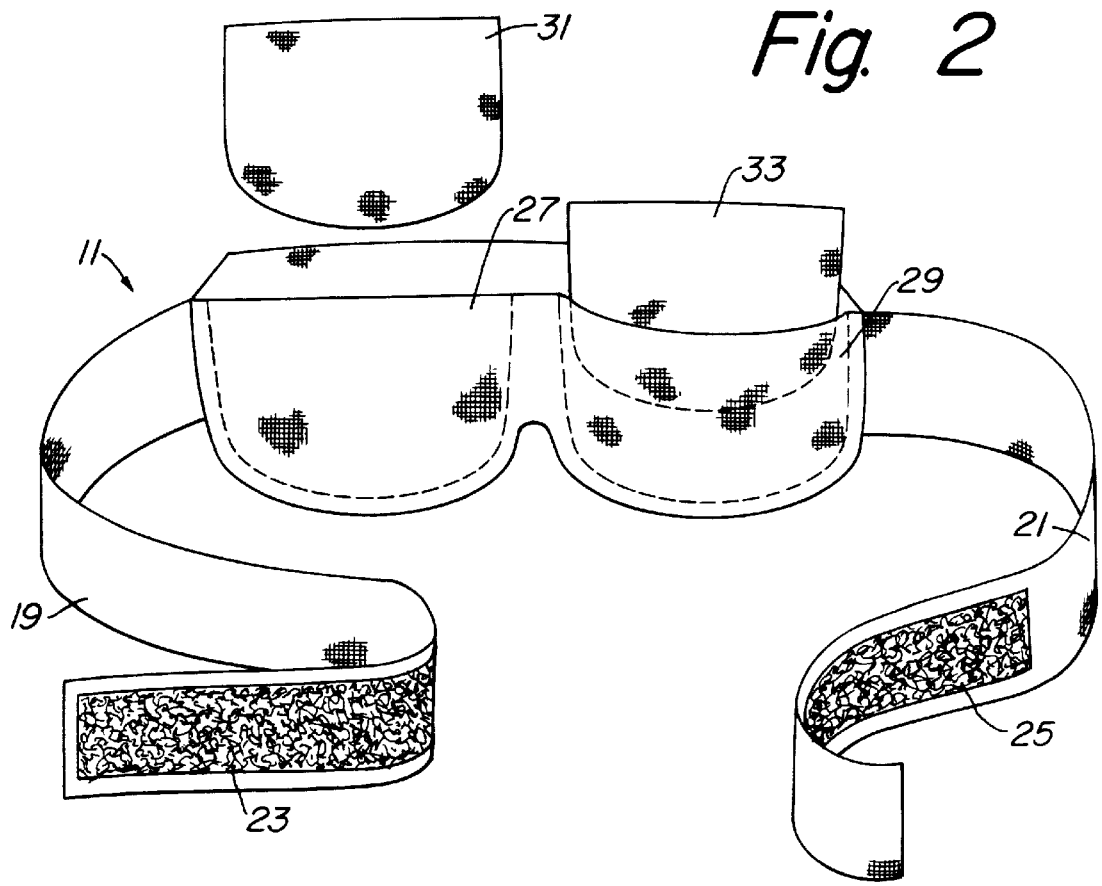
FIG. 2 is a perspective rear-view of the face mask showing a facial contact element being placed within the pocket means.

Referring to FIG. 2 is shown the facial contact elements 31 and 33 of the invention. These facial contact elements 31 and 33 are reversibly placed within the pocket means 15 and 17. The facial contact elements can be either pre-made elements such as permeable fabric bags, or other items used for cosmetic and therapeutic applications such as slices of vegetables and fruits (cucumbers, etc.). Also, the pocket means 15 and 17 can be used to hold hot or cold elements within, the elements then serving to either heat or cool the person's skin and tissues beneath the skin. The facial contact elements used as permeable sealed fabric bags typically contain various cosmetic, aromatherapy, or therapeutic materials, described further below.

Referring further to FIG. 2 is shown the straps 19 and 21 having fastening means 23 and 25, respectively. In one embodiment, the fastening means is a sewn-in hook-and-loop material that is easily adjustable to various sized head diameters. Other fasteners include buttons or a continuous strap between 19 and 21 that is elastic, thus forming a continuous loop of material to go around a person's head, and holding the facial contact elements 31 and 33 firmly against the person's skin.

The mask 11 is typically worn by a person as a carrier for therapeutic, cosmetic, or hot or cold elements. A typical therapeutic application would be as a carrier for aromatherapy oils and substances, the substances being placed within the permeable fabric bags serving as facial contact elements. Typically, a therapeutic oil or number of oils are diluted with a carrier oil and placed in the bags 31 and 33. Solid beads can also be used to hold the oils, those beads or seeds also being placed in the bags 31 and 33.

There are a number of aromatherapy oils that can be used in the bags 31 and 33. The oils are extracted from various species of plants, then often distilled to purify the oil to its essential component. Oils that are used in the facial contact element bags of the invention include but are not limited to (common names) angelica root, anise, balsam, basil, bay, bay laurel, beeswax, benzoin, bergamot, bois-de-rose, cajeput, carrot seed, cedarwood, chamomile, cinnamon, citronella, clary sage, clove bud, cypress, dill, elemi, eucalyptus, fennel, frankincense, galbanum, geranium, ginger, hyssop, jasmine, juniper berry, lavender, lavendin, lemon, lemongrass, lime, linden blossom, marjoram, myrrh, neroli, nutmeg, oakmoss, olibanum, orange, palmarosa, parsley, patchouli, pepper, peppermint, petitgrain, scotch pine, rose, rosemary, sandalwood, spearmint, spruce, tagetes, tangerine, tee tree, thyme, tobacco, vanilla, vetiver, yarrow, and ylang ylang. Examples of carrier oils used to dilute the aromatherapy oils are almond, apricot kernel, grapeseed, avocado, peanut, olive, pecan, macadamia nut, evening primrose, sesame, wheat germ and walnut oils. One or a combination of carrier oils may be used. The aromatherapy oils may be diluted to between about 0.1% and 30% typically, or used in mixtures undiluted. Also, there may be stabilizers present in the oils such as α-tocopherol (vitamin E) or citrate.

The material used to make the sealed fabric bags 31 and 33 that contain the aromatherapy oils should be gas permeable. Materials such as cotton or silk are preferable, but synthetic fabric materials such as nylon or polyester may also be used. The bags 31 and 33 containing the oils are placed in pocket means 27 and 29, then the mask 11 is placed onto the head with the eye patch regions 15 and 17 against the person's eyes and surrounding area. The straps having fastening means is used to secure the mask to the person's head, the straps adjusted to firmly hold the bags or other facial contact elements against the person's skin.

The present invention has many advantages over the prior art. The facial mask of the present invention is completely washable, which is important for an item that is held in place against a person's skin, and which also holds items such as therapeutic oils and the like, all of which may soil the material. The materials used to make the facial mask may be either hand washed or machine washed easily.

Another advantage to the present facial mask is that it provides a means for easily changing out one facial contact element for another, such as an aromatherapy bag or a cold compress. Also, if desired, different materials may be placed in one pocket means relative to the other. Most facial masks in the prior art do not allow such versatility.

Another advantage to the present invention is that the permeable nature of the facial mask and bags allows for the oils within the aromatherapy bags to be breathed in by the person wearing the mask as well as absorbed through the skin around the eyes. This is not possible when the mask is made from a non-permeable material such as plastic, PVC, and the like. Thus, the facial mask of the present invention may serve a dual purpose.

While the invention has been shown in only one of its forms, it is not thus limited but is susceptible to various changes and modifications without departing from the spirit thereof.

What is claimed is:

1. A washable facial mask for use in contact with a person's skin, the facial mask comprising:
    a unitary frontal element having an outer surface and an inner surface and having two integral eye patch regions made from a washable material, the two eye patch regions coupled to straps having a fastening means for securing the eye patch regions over the eyes of a person, the straps being made from a washable material;
    wherein the eye patch regions have a pocket means formed on the inner surface, each pocket means comprising a generally rectangular region with a top edge, a bottom edge and opposing side edges, each of a given length, the top edges of each of the pocket means forming an opening to an internal volume at the top of each pocket means substantially along the length thereof for allowing placement, of facial contact elements, the pocket means also made from a washable material;
    a facial contact element located within each pocket means;
    wherein the pocket means is made from a permeable synthetic mesh material of such a porosity as to allow free permeability of gases and moisture between the mesh in communication between the person's skin and facial contact elements within the pocket means; and
    wherein the facial contact elements are sealed fabric bags which are sized to fit within the pocket means and to substantially occupy the internal volume of the pocket means, the bags containing a therapeutic aromatherapy material.

2. The mask of claim 1, wherein the eye patch regions are opaque.

3. The mask of claim 1, wherein the fastening means is hook-and-loop material.

4. The mask of claim 1, wherein the facial contact elements are variable temperature elements.

5. The mask of claim 1, wherein the washable material is selected from a group comprising silk, nylon, satin and cotton.

6. A washable facial mask for use in contact with a person's skin, the facial mask comprising:
    a unitary opaque frontal element having an outer surface and an inner surface and having two integral eye patch regions made from material selected from a group comprising nylon, silk, satin and cotton, the two eye patch regions coupled to straps having a fastening means for securing the eye patch regions over the eyes of a person, the straps being made from a washable material;
    wherein the eye patch regions have a pocket means formed on the inner surface, each pocket means comprising a generally rectangular region with a top edge, a bottom edge and opposing side edges, each of a given length, the top edges of each of the pocket means forming an opening to an internal volume at the top of each pocket means substantially along the length thereof for allowing placement of facial contact elements, the pocket means also made from a washable material;
    a facial contact element located within each pocket means;
    wherein the pocket means is made from a permeable nylon mesh material of such a porosity as to allow free permeability of gases and moisture between the mesh in communication between the person's skin and facial contact elements within the pocket means; and
    wherein the facial contact elements are sealed fabric bags which are sized to fit within the pocket means and to substantially occupy the internal volume of the pocket means, the bags containing a therapeutic aromatherapy material selected from the group consisting of aromatic oils and aromatic beads.

7. The mask of claim 6, wherein the fastening means is hook-and-loop material.

8. The mask of claim 6, wherein the facial contact elements are variable temperature elements.

* * * * *